United States Patent [19]

Vonvoigtlander et al.

[11] Patent Number: 4,801,604
[45] Date of Patent: Jan. 31, 1989

[54] CIS-N-(2-AMINOCYCLOALIPHATIC)BENZAMIDE ANTI-CONVULSANTS

[75] Inventors: Philip F. Vonvoigtlander, Plainwell; Jacob Szmuszkovicz, Kalamazoo, both of Mich.

[73] Assignee: The Upjohn Company, Kalamazoo, Mich.

[21] Appl. No.: 76,411

[22] Filed: Jul. 21, 1987

Related U.S. Application Data

[63] Continuation-in-part of Ser. No. 791,311, Oct. 25, 1985, abandoned and Continuation-in-part of PCT US86/02228, Oct. 21, 1986, abandoned.

[51] Int. Cl.⁴ .................. A61K 31/40; C07D 295/06
[52] U.S. Cl. ..................... 514/429; 548/578
[58] Field of Search ............. 514/429; 548/578

[56] References Cited

U.S. PATENT DOCUMENTS

| | | | |
|---|---|---|---|
| 4,098,904 | 7/1978 | Szmuszkovics | 544/400 X |
| 4,145,435 | 3/1979 | Szmuszkovics | 544/400 X |
| 4,463,013 | 7/1984 | Collins et al. | 548/407 X |

OTHER PUBLICATIONS

Tortella, et al.; J. of Pharm. & Exp. Therapeutics, 237 (1986), pp. 49–53.
Tortella, et al., Neuroscience Abstracts, 10 (1984), p. 408.
Clark, et al., J. Med. Chem. 27 (1984), pp. 779–782.
Berman, Neuropharmacology, 23, No. 3, (1984), pp. 367–371.
The Merck Index, 10th Ed. (1983), item 7204.

Primary Examiner—Joseph Paul Brust
Attorney, Agent, or Firm—John T. Reynolds

[57] ABSTRACT

Certain cis-N-(2-amino-cycloalophatic)benzamides of the formula

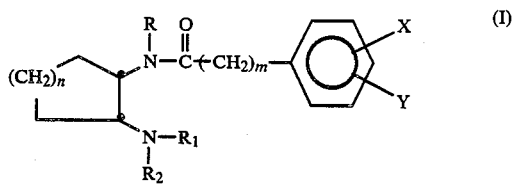

where m is 0, n is 2, r is alkyl, $R_1$ and $R_2$ are taken together with the nitrogen denote a pyrrolidine ring, X and Y are hydrogen or a halogen having an atomic number of from 9 to 35, e.g., cis-3,4-dichloro-N-methyl-n[2-(1-pyrrolidinyl)cyclohexyl]benzamide, and salts thereof, have been found to have CNS seizure blocking or preventing drug action, e.g., anti-convulsant drug properties with little or no analgesic properties.

6 Claims, No Drawings

CIS-N-(2-AMINOCYCLOALIPHATIC)BENZAMIDE ANTI-CONVULSANTS

CROSS-REFERENCES

This is a continuation-in-part of International Application No. PCT/US86/02228 filed Oct. 21, 1986 and U.S. application Ser. No. 791,311 filed Oct. 25, 1985 both now abandoned, the priority of which applications is hereby claimed.

INTRODUCTION

This invention relates the use of certain N-(2-aminocycloaliphatic)benzamide compounds as Central Nervous System (CNS) antiseizure, e.g., anti-convulsant, drugs in valuable warm-blooded animals, including humans.

BACKGROUND OF THE INVENTION

Szmuszkovicz U.S. Pat. No. 4,098,904 discloses some N-(2-aminocycloaliphatic)benzamide compounds, e.g., N-methyl-N-[2-(1-pyrrolidinyl)cyclohexyl]-3,4-dichlorobenzamide and N-methyl-N-[2-(N',N'-dimethylamino)cyclohexyl]-4-bromobenzamide, and salts and hydrates thereof as analgesic (pain reducing) drug compounds.

Szmuszkovicz U.S. Pat. No. 4,145,435 discloses some 2-aminocycloaliphatic alkanoyl amide compounds, e.g., N-methyl-N-[2-(N',N'-dimethylamino)cyclohexyl]-2-(4-bromophenyl)acetamide and trans-2-(3,4-dichlorophenyl-N-methyl-N-[2-(1-pyrrolidinyl)cyclohexyl]acetamide and their pharmaceutically acceptable salts as analgesic compounds.

In contrast to the disclosures of those '904 and '435 patents, the compounds of this invention have little or no significant analgesic activity ($ED_{50} > 50$ mg/kg), but have been found to possess significant CNS seizure preventing or blocking activity in standard laboratory animal tests.

In *Neuroscience Abstracts*, 10, page 408 (October, 1984), F. C. Tortella et al report the seizure-specific, dose- and Time-dependent Anti-convulsant Profile of Upjohn Compound, trans-($\pm$)-3,4-dichloro-N-methyl-N-[2-(1-pyrrolidinyl)cyclohexyl]benzeneacetamide by an electrshock method. This compound is described and claimed in the above Szmuszkovicz '435 patent; however, as indicated hereinabove, this compound is an analgesically active compound.

Recent pharmacology articles that may be of interest as background are:

*J. Med. Chem.*, 1984, 27, pp. 779–782, "Anticonvulsant . . . 4-Aminobenzamides" by C. Randall Clark, et al.;

*Science*, 226, Nov. 16, 1984, pp. 850–852, "Blockade . . . Against Ischemic Damage in the Brain", by R. P. Simon et al, and

*Neuropharmacology*, 23, No. 3, pp. 367–371 (1984), "The Anticonvulsant . . . Electroshock Seizures in Rats" by E. F. Berman et al, although these references are not conceded to be prior art to the invention described and claimed herein.

OBJECTS OF THE INVENTION

It is an object of this invention to provide some new N-(2-aminocycloaliphatic)benzamide compounds, which compounds have been found to have significant CNS seizure preventing and blocking activity, while having little or no analgesic activity.

It is a further object of this invention to provide a method for preventing or blocking CNS seizures in warm-blooded valuable animals, including humans, with certain N-(2-aminocycloaliphatic)benzamide drug compounds.

Another object of this invention is to provide pharmaceutical compositions useful in dosage unit forms for administration to valuable warm-blooded animal patients, including humans, for prevention or blocking of CNS seizures in such patients.

Other objects, aspects and advantages of the invention will be apparent from reading the remaining specification and the claims which follow.

SUMMARY OF THE INVENTION

Briefly, this invention provides some new cis-N-[(2-aminocycloaliphatic)benzamide compounds of general formula I and their pharmaceutically acceptable salts, which compounds have been discovered to have significant CNS seizure-preventing activity while also showing only minimal, non-significant or no analgesic activity, at the highest dose tested, in standard laboratory animal tests.

The invention also includes pharmaceutical compositions containing at least one of these compounds and a method for treating warm-blooded animal patients, including humans, with these compositions to prevent or block CNS seizures of various types in such patients.

DETAILED DESCRIPTION OF THE INVENTION

The group of compounds described herein have been found to be effective anti-convulsant drug agents in standard animal tests. These compounds have been shown to be effective antagonists of electroshock seizures in mice. They will be useful in the treatment of grand mal and other seizure disorders in man as well as in commercially important and pet animals.

These compounds are active in the CNS electroshock animal test but they did not at similar dosage ranges block chemically-induced (pentylenetetrazol or bicucullin) seizures in the test animals suggesting that these compounds have a CNS anti-seizure utility similar to that of the known drug phenytoin (*THE MERCK INDEX*, 10th Edition, page 1054, item 7204). Phenytoin is useful in the treatment of grand mal, focal and psychomotor seizures (see Goodman and Gilman, *The Pharmacological Basis of Therapeutics*). However, phenytoin and structurally related anti-convulsant drugs are known to cause a number of side effects including hyperplasia of the gums, cerebellar degeneration, gastric distress and serious skin rashes.

In contrast, the compounds of this invention, while being antiseizure drugs, e.g., anti-convulsant drugs at reasonable dosages, have little or no significant analgesic activity, and it is also hoped that these cis-compounds will not show some of the other above-listed side effects as well. The anti-convulsant potency of these cis-amino-benzamide compounds in standard laboratory animal tests indicate that these compounds will be useful for preventing or treating CNS seizure disorders in warm-blooded animals such as cats, dogs, horses, as well as humans at dosage ranges of approximately 0.1 to 100 mg./kg. of body weight/day via the oral or parenteral routes until the seizure threat or attack subsides.

The compounds of this invention of formula I in the GENERAL FORMULAS hereinbelow are cis-N-[(2-aminocycloaliphatic)benzamide compounds where the two large filled circle positions in the ring are intended to depict the cis orientation of the two nitrogen groups relative to each other and the ring, n is 2, to indicate a cyclohexyl ring;

m is 0, to indicate that the compounds are benzamides (without the —CH$_2$—);

R is C$_1$ to C$_3$-alkyl, e.g., methyl, ethyl, isopropyl or n-propyl, preferably methyl;

R$_1$ and R$_2$ are taken together with the nitrogen to which they are bonded to complete a pyrrolidine ring;

X and Y are each hydrogen or a halogen having an atomic number of from 9 to 35, that is fluorine, chlorine or bromine, preferably chlorine, in the 3- and the 4-positions or bromine in the 4-position;

or a pharmaceutically acceptable salt thereof.

Acid addition salts of these amino-amide (I) compounds can be prepared by reacting a formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicylic acid, pamoic acid, cyclohexanesulfamic acid, methanesulfonic acid, naphthalenesulfonic acid, p-toluenesulfonic acid, maleic acid, fumaric acid, oxalic acid and the like. Nonaqueous media are preferred.

On occasion the compounds (I) or their acid addition salts in their crystalline state are isolated as solvates, e.g., with a discrete quantity of solvent, e.g., water, methanol, and the like, associated physically, and thus not affecting the chemical entity per se.

This invention also relates to compositions containing a formula I compound as an active ingredient in a pharmaceutical carrier. The compositions are useful in pharmaceutical dosage unit forms of the formula I compound for systemic administration (oral, rectal, parenteral, including intravenous, intramuscular and intra-arterial administration form) for treating warm-blooded animal patients, cats, dogs, horses and other commercially valuable animals, and human patients suspected of being susceptible to or to stop CNS seizures, such as convulsions, grand mal, petit mal and other seizure disorders. The term "dosage unit form" as used in this specification and in the claims refers to physically discrete units suitable as unitary dosages for mammalian subjects, each unit containing a predetermined quantity of the essential active ingredient compound of this invention calculated to produce the desired effect in combination with the required pharmaceutical means which adapt the said ingredient for topical or systemic administration. The specifications for the novel dosage unit forms of the invention are indicated by and directly dependent on the physical characteristics of the essential active ingredient and the particular effect to be achieved in view of the limitations inherent in the art of compounding such an essential active material for beneficial effects in humans and animals. Examples of suitable dosage unit forms in accordance with this invention are tablets, capsules, orally administered liquid preparations in suitable liquid vehicles, sterile preparations in suitable liquid vehicles for intramuscular and intravenous administration, supositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled a composition of these amino-benzamide active ingredient in combination with suitable diluents nd excipients, for example, edible oils, talc, calcium carbonate, and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases it is preferable to include osmotically active agents, for example, sugars and sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance the preceding general description to provide from about 1.0 to about 700 mg. of the essential active ingredient per dosage unit form, which as aforesaid may be in the form of a solid, semi-solid, topical, oral or rectal preparation, a liquid oral preparation, an injectable preparation, including liquid preparation and dry solid preparations for extemporaneous reconstitution to a liquid injectable preparation. The amount of the essential active ingredient provided in the pharmaceutical dosage unit forms is that amount sufficient to obtain a reduction in the CNS seizure effects and a return to more normal CNS stability, or to prevent the occurrence of CNS seizures in a patient who is suspected to be subject to such seizure. Expressed otherwise, an amount of the essential active ingredient is provided to a recipient within a range of from about 0.1 mg. per kg. to about 100 mg. per kg. of body weight of the recipient. Preferred dosages for most applications are 1.0 to 10.0 mg. per kg. of body weight.

The useful dosage unit forms of these compounds in pharmaceutical formulations is preferably adapted for systemic administration to obtain anti-convulsant effects comprising an effective, non-toxic amount of a compound according to formula I or as its pharmacologically acceptable salt. Further, the invention relates to methods of obtaining such CNS anti-seizure effects in mammals, for example, humans and valuable warm-blooded animals such as dogs, cats, horses and other commercially valuable animals, by administering systemically to the mammals the aforesaid pharmaceutical dosage unit forms supplying an effective, non-toxic amount for anti-convulsant effects.

These specific cis-amino-benzamide compounds have an advantage, to a greater or lesser extent, depending upon the particular compound, of having significant CNS anti-seizure properties, while having little or no significant analgesic activity (analgesic $ED_{50}>50$ in the HCl writhing analgesic test). This combination of properties should prove beneficial and advantageous where the doctor would prefer to treat the patient for the single CNS seizure disorder without need to worry about any significant analgesic side effects.

The cis-amino-benzamide compounds involved in this invention can be made by procedures described in the Szmuszkovicz U.S. Pat. No. 4,098,904, supra, using the cis-1,2-diamines referred to in that patent, and the appropriate acylating form of the selected benzoic acid, benzoyl halide, as described generally therein. Described hereinbelow are procedures used to prepare the compounds described and exemplified herein. SCHEME I and II attached hereto, show a typical procedure for preparing the compounds involved in this invention.

Scheme I outlines in general chemical symbol form a process for preparing cis-diamine starting materials, which can be used to make the cis-2-amino-cycloaliphaticbezamide compounds, which are used according to the invention described herein.

In general, the alkyl cycloalkanone carboxylate ester starting material (II), which can be, e.g., the pure methyl, ethyl or propyl esters or the commercially available mixed esters, and the selected $HNR_1R_2$ amine, e.g., pyrrolidine, are mixed and reacted in a selected solvent such as benzene, toluene, heptane, or the like, while heating under reflux conditions to remove water by-product from the reaction mixture to form the respective alkyl 2-aminocycloalk-1-enyl-carboxylate ester (III). Alternately, the alkyl 2-amino-cycloalk-1-enylcarboxylate ester (III) can be prepared from a 1-cycloalkenylamine (IV) and a carboxylation agent.

The resulting 2-aminocycloalk-1-enylcarboxylate ester (III) can then be reduced, e.g., by hydrogenating the reaction mixture containing the ester (III) in the presence of a hydrogenation catalyst such as platinum oxide to form the saturated cis-2-aminocycloaliphatic ester (V).

For compounds where R is to be a $C_1$ to $C_3$-alkyl, the cis-2-aminocycloalkylamine (VII) is further acylated with an alkyl formate (to form an R equals methyl compound, or with an acetyl halide or propionyl halide, e.g., acetyl chloride or propionyl chloride, in the presence of a tertiary amine hydrogen halide scavenger to form the cis-N-(2-aminocycloalkyl) $C_1$ to $C_3$-alkanoylamide (VIII), where $R_3$ is hydrogen or $C_1$ to $C_2$-alkyl. This resulting amino-amide (VIII) can then be subjected to carbonyl group reduction, e.g., with lithium aluminum hydride to convert the R—C(O)— group on the nitrogen in the 1-position of the cycloalkyl ring to the defined R equals $C_1$ to $C_3$ alkyl group and to form cis-diamine (IX).

Scheme II describes in chemical symbol form an amine nitrogen acylation process that can be used to make the cis-N-[2-(aminocycloaliphatic)benzamide (m=0) compounds which can then be recovered from their reaction mixtures, and used according to this invention or converted to appropriate acid addition salt form for recovery from its reaction mixture, and then re-formed, if desired or necessary, into an appropriate, pharmaceutically acceptable acid addition salt form for compounding into appropriate marketing and dosage unit forms.

Here, in Scheme II the cis-cycloaliphatic diamine (IX) can be acylated by known procedures, e.g., by reaction with a benzoyl halide (X), in the presence of a tertiary amine hydrogen halide scavenger, such as triethylamine or N,N-dimethylaniline, to form the N-[2-(aminocycloalkyl)-N-alkylbenzamide. These latter compounds can then be processed as indicated herein to put the compounds in pharmaceutically acceptable useful form.

Preparation of Cis-2-Pyrrolidinylcyclohexylamine

This preparation exemplifies how cis-1,2-cyclohexaneamines were prepared for use in preparing the cis-amino-benzamide compounds which are involved in the invention described and claimed herein.

A. Ethyl cis-2-pyrrolidinylcyclohexanecarboxylate

A solution of 164.4 g. (1.0 mole) of ethyl 2-cyclohexanone carboxylate (also named ethyl 2-oxocyclohexanoate), which also contained about 40 percent of the corresponding methyl ester, and 71.1 g. (1.0 mole) of pyrrolidine in 700 ml. of benzene was refluxed overnight with azeotropic distillation of water therefrom (18 ml $H_2O$ collected) to form the ethyl and methyl 2-(1-pyrrolidinyl)-1-cyclohexen-1-ylcarboxylate mixed ester. Then 10 g. of platinum oxide was added to this resulting reaction mixture and the mixture was hydrogenated at 30 psig. until uptake of hydrogen ceased. About 0.95 mole of hydrogen was consumed. The resulting hydrogenated reaction mixture contained the cis-ethyl and methyl mixed 2-(1-pyrrolidinyl)cyclohexanecarboxylate esters. This reaction mixture was filtered through a filter aid (CELITE ®) to remove the platinum catalyst residue. The filtered liquid was then extracted with 200 ml. of 6N hydrochloric acid. The resulting aqueous layer was washed with ether, made basic with 15 percent sodium hydroxide solution and again extracted with ether. The original organic layer and the ether wash were combined as one organic layer and washed with saturated sodium chloride in water solution, dried ($MgSO_4$) and evaporated to remove solvents. Distillation of the residue gave the cis-2-(1-pyrrolidinyl)cyclohexanecarboxylate, mixed methyl and ethyl esters, 143.5 g. (70 percent yield, b.p. 95°–105° C./0.5 mm. Hg.)

This cis-amino-cyclohexanecarboxylate mixed ester material was used in the next step of the process without further purification.

B. Cis 2-Pyrrolidinylcyclohexanecarboxhydrazide and its hydrochloride.

A solution of 143.5 g. (0.65 mole) of the named amino-mixed ester material from Part A hereinabove and 162.5 g. (3.25 moles) of hydrazine hydrate in 1300 ml. of absolute ethanol was stirred at room temperature for 24 hours, and then refluxed for 72 hours to form the 2-(1-pyrrolidinyl)cyclohexanecarboxhydrazide. The solvent was largely removed by evaporation. The residue was diluted with 1500 ml. of methylene chloride, washed twice with 150 ml. portions of saturated aqueous sodium chloride solution, dried ($MgSO_4$) and evaporated to remove most of the methylene chloride.

The 2-(1-pyrrolidinyl)cyclohexanecarboxhydrazide hydrochloride salt was prepared by treatment of his hydrazide residue with hydrogen chloride in ether solution and was crystallized from a methanol/ether solvent mixture to give the cis-2-(1-pyrrolidinyl)cyclohexanehydrazide hyrochloride, 126.8 g., (69 percent yield) m.p. 222°–224° C. The UV, mass spectrum, IR and NMR spectra were consistent with this named compound.

Anal. Calcd. for $C_{11}H_{21}N_3O \cdot 2HCl$: % Calcd.: C, 46.48; H, 8.16; N, 14.78; Cl, 24.95; % Found: C, 45.49; H, 8.22; N, 15.20; Cl, 25.50.

C. Cis-2-(1-pyrrolidinyl)cyclohexaneamine

To a solution of 53.4 g. (0.188 mole) of the 2-(1-pyrrolidinyl)cyclohexanecarboxhydrazide hydrochloride in 100 ml. of water, prepared as in part B hereinabove with ice cooling there was added 14.3 g. (0.207 mole) of sodium nitrite in 25 ml. of water over 30 minutes while stirring. After 30 minutes 30 ml. of 12N hydrochloric acid was added to the reaction mixture and the solution was slowly heated to 70° on a water bath. When evolution of nitrogen by-product had nearly ceased, the solution was heated on a steam bath for one hour. The resulting solution was cooled, made basic with 15 percent sodium hydroxide solution and extracted with ether. The ether extract was dried ($MgSO_4$) and evaporated to remove solvent. distillation of the residue gave 25.7 g. (81 percent yield) of the diamine, cis-2-(1-pyrrolidinyl)cyclohexaneamine, b.p. 120°–123° C./14 mm. (Hg.). The UV, IR, NMR and mass spectra were consistent with this named compound.

Anal. Calcd. for $C_{10}H_{20}N_2$: % Calcd.: C, 71.37; H, 11.98; N, 16.65; % Found: C, 71.05; H, 11.91; H, 16.49.

D. N-methyl-Cis-2-(1-pyrrolidinyl)cyclohexylamine

A solution of 20.0 g. (0.119 mole) of the cis-2-(1-pyrrolidinyl)cyclohexaneamine from Part C above kin 250 ml. of ethyl formate solvent was refluxed overnight. The solution was evaporated to remove solvent and leave a crude amide intermediate as a colorless oil product. The crude product was dissolved in 100 ml. of tetrahydrofuran (THF) and added dropwise in one hour to a suspension of 20.0 g. of lithium aluminum hydride in 1000 ml. of ether. The mixture was refluxed for six hours and then kept overnight at room temperature. The mixture was cooled in ice and excess lithium aluminum hydride was decomposed by adding 20 ml. of water, 20 ml. of 15 percent sodium hydroxide aqueous solution and 60 ml. of water. The mixture was filtered and the filtered by-product aluminum salt solids were washed with ether. The filtrate and ether washings were dried ($MgSO_4$) and evaporated to remove solvents. Distillation of the residue gave 16.5 g (76 percent yield) of the cis-N-methyl-N-[2-(1-pyrrolidinyl)cyclohexaneamine, b.p. 120°–122° C./14 mm. (Hg.). The UV, IR, NMR and Mass Spectra were consistent with this named compound.

Anal. Calcd. for $C_{11}H_{22}N_2$: % Calcd.: C, 72.46; H, 12.17; N, 15.37; % Found: C, 72.64; H, 12.73; N, 15.42.

EXAMPLE 1

Cis-N-[2-(N',N'-dimethylamino)cyclohexyl]benzamide

To a mixture of 1.42 g. (0.01 mole) of cis-[2-(dimethylamino)cyclohexyl]amine (prepared as described in U.S. Pat. No. 4,098,904, starting at column 21, line 67) and 1.01 g. (0.01 mole) of triethylamine in 100 ml. of diethyl ether there was added 1.41 g. (0.01 mole) of benzoyl chloride in 25 ml. of ether over 30 minutes with ice cooling of the reaction vessel. The reaction mixture was stirred overnight at room temperature. Then 100 ml. of a saturated sodium bicarbonate in water solution was added to the resulting reaction mixture. The aqueous layer was separated from the organic liquid layer. The organic liquid layer was then washed with brine (saturated aqueous sodium chloride), separated from the aqueous brine layers and dried using anhydrous magnesium sulfate and then evaporated to remove solvent and to leave a yellow oil residue, which residue became solid on standing, and which weighed 2.43 g. (99 percent, crude yield) of the cis-N-[2-(dimethylamino)cyclohexyl]-N-benzamide, m.p. 73°–76° C.

The hydrochloride salt of this cis-N-[2-(dimethylamino)cyclohexyl]benzamide was made by dissolving this amino-amide compound in excess hydrogen chloride in ether solution and then evaporating solvent therefrom to crystallize the hydrochloride salt therefrom. This amino-amide hydrochloride salt was recrystallized from a mixture of 10 ml. of methanol an about 40 ml. of ether to obtain 2.13 g. (75 percent yield) of the cis-N-[2-(dimethylamino)cyclohexyl]benzamide hydrochloride, m.p. 247°–248° C.

The elemental analysis for this amino-amide salt was:
Anal. Calcd. for $C_{15}H_{22}N_2O \cdot HCl$ (282.81): % Calcd.: C, 63.70; H, 8.20; N, 9.91; Cl, 12.54; % Found: C, 63.90; H, 8.53; N, 9.92; Cl, 12.69.

The nucler magnetic resonance (NMR) spectrum ($D_2O$) was consistent for this named product. The infrared (IR) spectrum was also consistent. The ultraviolet (UV) light spectrum showed (ethyl alcohol) end absorption 227 (11,650); 226 sh (846), 269 (769). The mass spectrum showed a main ion of M+246.

Following procedures known in the art or as described hereinabove the following additional examples of these cis-amino-amide compounds were prepared:

EXAMPLE 2

Cis-3,4-dichloro-N-N-methyl-N-[2-(1-pyrrolidinyl)cyclohexyl]benzamide, and its monohydrochloride.

M.P.: 229° C. (methanol/ether

Anal. Calcd. for $C_{18}H_{24}Cl_2N_2O \cdot HCl$: % Calcd.: C, 55.18; H, 6.43; N, 7.18; Cl, 27.15; % Found: C, 55.43; H, 6.50; N, 7.18; Cl, 27.49.

EXAMPLE 3

Anti-convulsant Use Test Results—Electroshock Test

This example exemplifies anti-convulsant activity properties of representative compounds of this invention in a standard laboratory animal electroshock test.

Male CF-1 mice were injected subcutaneously with the test compound and after the compound was absorbed, the test mice were subjected to maximal transpinal electroshock (10 mA, 0.2 sec.). Protection from central nervous system (CNS) seizure by the test compound was judged by the absence of the tonic extensor convulsion. Each test drug substance or compound was formulated into 0.25 percent w/v aqueous methylcellulose solution and administered at a volume dose of 10 ml. per kilogram of body weight. A group of six mice was treated and tested at each dose level, and decreasing doses (0.3 log intervals) were administered to such groups of mice until response activity was low enough so that $ED_{50}$ dose calculations within 95 percent confidence intervals could be established. Most of these exemplified compounds lack any significant analgesic activity ($ED_{50}$ greater than 50 in standard HCl writhing analgesic test).

TABLE I

Electroshock Test Results
($ED_{50}$, subcutaneous route, mg./kg.)
(95 percent, Confidence Index Range)

| Example No. Compound | Electroshock ($ED_{50}$, mg./kg.) |
|---|---|
| 2 | 13 (9-17) |

EXAMPLE 4

One thousand tablets for oral use, each containing 175 mg. of cis-3,4-dichloro-N-methyl-N-[2-(1-pyrrolidinyl)-cyclohexyl]benzamide hydrochloride as the essential active ingredient, are prepared from the following ingredients:
Essential active ingredient: 175 g.
methylcellulose, U.S.P. (15 cps.)—6.5 g.
talc—20 g.
calcium stearate—2.0 g.

The essential active ingredient and dicalcium phosphate are mixed well, granulated with 7.5 percent aqueous solution of methylcellulose, passed through a No. 8 screen and dried carefully. The dried granules are passed through a No. 12 screen mixed with the talc and stearate and compressed into tablets. These tablets are useful in the treatment of adult humans at a dose of one tablet one to four times a day as needed to prevent convulsions.

EXAMPLE 5

One thousand two-piece hard gelatin capsules for oral use, each capsule containing 100 mg. of cis-3,4-dichloro-N-methyl-N-[2-(1-pyrrolidinyl)cyclohexyl]-benzamide hydrochloride as the essential active ingredient, are prepared from the following ingredients:
Essential active ingredient—100 g.
Lactose, U.S.P.—100 g.
Starch, U.S.P.—10 g.
Talc, U.S.P.—5 g.
Calcium stearate—1 g.

The finely powdered materials are mixed thoroughly and then filled into hard gelatin capsules of appropriate size.

One capsule four times a day is useful for the treatment of adult humans to block the occurrence of CNS convulsive seizures.

EXAMPLE 6

A sterile aqueous suspension suitable for intramuscular injection and containing in each milliliter 50 mg. of the Example 5 essential active ingredient is prepared from the following ingredients:
Essential active ingredient—5 g.
Polyethylene glycol 4000, U.S.P.—3 g.
Sodium chloride—0.9 g.
Polysorbate 80, U.S.P.—0.4 g.
Sodium metabisulfite—0.1 g.
Methylparaben, U.S.P.—0.18 g.
Propylparaben, U.S.P.—0.02 g.
Water for injection, q.s. to—100 ml.

The preceding sterile injectable is useful in the treatment of CNS convulsions in adult humans at a dose of ½ to 2 ml.

EXAMPLE 7

CNS Identification (Primary or Preliminary) Test

The four listed compounds were tested in a CNS identification screen test in a prelimiary hydrochloric acid (HGl) writhing test, described just below, to determine if the respective test compounds show any preliminary indication of CNS analgesic activity. Antagonism of HCl-Induced Writhing:

Groups of four male albino CF-1 mice (18-22 g. each) were injected subcutaneousluy with the test agent prepared in 0.25 percent methylcellulose. Thirty minutes later the mice are challenged with a 0.15 percent HCl solution administered intraperitoneally at 10 ml./kg. The mice are then placed in separate plastic boxes (10 cm × 12.7 cm) and observed over the following fifteen minutes for writhing. A compound is considered active if at least three animals in the group are protected from writhing. $ED_{50}$ values are then calculated by the method indicated below.

The Electroshock Anti-convulsant Activity Test

Method:

Male CF-1 (Carworth Farms) mice were injected subcutaneously with the test compunds and, after the indicated absorption time, subjected to maximal transpinal electroshock (10 mA, 0.2 sec). Protection from seizure was judged by the absence of the tonic extensor convulsion. The drugs were formulated in aqueous methylcellulose and administered at a volume dose of 10 ml./kg. Six mice were treated and tested at each dose level and decreasing doses (0.3 log intervals) were administered to establish $ED_{50}$ values and 95 percent confidence intervals thereof.

Analgesic Tests

Female CF-1 derived Upjohn mice, 18 to 22 grams each, were used, six animals per group. A solution or suspension of the test compound in the above indicated vehicle was administered subcutaneously, 11 mg./kg., and fifteen minutes following dosing, the following series of procedures were carried out.

Tail Flick Test

A high intensity light is directed at the middle third of the test animals' tails simultaneous with the start of a photoelectric timer. The number of seconds required for the animal to "flick" its tail out of the light is recorded.

Tail Pinch Test

A bulldog arterial clamp is applied to the base of a test animal's test and the number of animals that do not turn within 30 seconds is recorded.

HCl Writhing Test

The test animals receive an intraperitoneal dose of 0.15 percent hydrochloric acid solution, one ml. per 100 g. of body weight. The number of animals failing to writhe in fifteen minutes is recorded.

The results of these three analgesic tests were expressed below in terms of the dose (calculated) with blocks the normal reflex in 50 percent of the animals ($ED_{50}$ values). These $ED_{50}$ values are calculated using the method of Spearman and Karber (Finney, D. J., "Statistical Method in Biological Assay", 1952, Hafner Publishing Co., New York, page 524).

The following known compounds can be expected to give the following $ED_{50}$ values in these same tests for analgesic effects:

| Compound | Tail Flick | Tail Pinch | HCl Writhing |
|---|---|---|---|
| Morphine sulfate | 1.5 | 1.6 | .6 |
| Pentazocine | 100 | 120 | 10 |
| Naloxone | >100 | >100 | >100 |

TABLE 1

| Test Compound | Name |
|---|---|
| 1 | Cis-3,4-dichloro-N—[2-(1-pyrrolidinyl)cyclopentyl]benzeneacetamide |
| 2 | Cis-3,4-dichloro-N—methyl-N—[2-(1-pyrrolidinyl)-cyclopentyl]benzamide |
| 3 | Cis-3,4-dichloro-N—[2-(1-pyrrolidinyl)cyclohexyl]benzamide |
| 4 | Cis 3,4-dichloro-N—methyl-N—[2-(1-pyrrolidinyl)-cyclohexyl]benzamide |

TABLE 2

| Test Compound | CNS Id ($ED_{50}$) (mg/kg) HCl Writhing Protect | Electro-Convulsive Shock Antagonism $ED_{50}$ (mg/kg) | Analgesic Screens $ED_{50}$ (mg/kg) SC | | |
|---|---|---|---|---|---|
| | | | Tail Flick | Tail Pinch | HCl Writhing |
| 1 | >50 | 50 | 63 | 71 | 71 |
| 2 | >50 | 32 | >100 | >100 | 63 |
| 3 | >50 | 18 | 45 | 45 | 45 |
| 4 | >50 | 13 | >100 | >100 | >100 |

CONCLUSIONS

The data in Table 2 for these test compounds (Table 1) indicate that each of the four compounds show useful ranges of CNS anticonvulsant activity and little, if any, analgesic activity and that compound 4 had no analgesic activity at the highest dose tested.

EXAMPLE 8

Upjohn's (Szmuszkovicz) U.S. Pat. Nos. 4,098,904 and 4,145,435, cited hereinabove, focused on the racemic cis-/trans- and then the trans-(±)- stereo structural configuration of those patented compounds which were of particular interest for their use for their analgesic property, and those patents emphasize that the useful analgesic properties of those classes of compounds resided in the trans-stereo configuration of the compounds.

The *Neuroscience Abstracts*, 10, page 408 (October, 1984) publication of T. C. Tortella et al entitled "SEIZURE SPECIFIC, DOSE AND TIME-DEPENDENT ANTICONVULSANT PROFILE FOR U-50,488, A NOVEL OPIOID-ANTAGONIST, IN RATS", reporting on their findings that U-50,488 was an efficacious long-acting anti-convulsant against the therein defined maximal electroshock stimuli, concluding that ". . . this structural novel opiate may represent a new class of therapeutically effective anti-grand mal agents."

As the Tortella et al publication discloses the Upjohn compound U-50,488 is named as trans-3,4-dichloro-N-methyl-N-[2-(1-pyrrolidinyl)cyclohexyl]benzeneacetamide. That acetamide compound was of primary interest as an analgesic lead compound because it was shown to have significant analgesic properties in standard laboratory animal tests, but, as shown in the Tortella et al publication, U-50,488 was found to also have anti-convulsant activity.

An electroshock test method for determining anti-convulsant drug activity of test substances is also described in the publication *NEUROPHARMACOLOGY*, 23, No. 3, pp. 367–371 (1984) in an article entitled "The Anticonvulsant Effect . . . Seizure In Rats" by E. F. Berman et al (copy made of record in this application).

In a similar anti-convulsant electroshock test in our laboratories we found that the compound U-54,494, cis-3,4-dichloro-N-methyl-N-[2-(1-pyrrolidinyl)cyclohexyl]benzamide, Compound 4 in Example 7 hereinabove, as its hydrochloride salt, which is claimed in this application for patent, was tested to determine its ability to block seizures induced in mice by maximal (10 mA, 0.2 sec.) electroshock, and it was found to have an $ED_{50}$ value of 13 mg/kg. which number indicates to us that the compound has significant anti-convulsant activity. After comparative tests with other compounds, this compound U-54,484, as one of its salts, has been selected for advanced laboratory testing as a possible clinical candidate compound as an anti-convulsant drug. The other cis- stereo configuration compounds, listed in Example 7 above, have been dropped from further advanced study as possible anti-convulsant drug candidate compounds.

The trans- stereo isomer compound of the above 3,4-dichloro-N-methyl-N-[2-(1-pyrrolidinyl)cyclohexyl]benzamide, U-53,739, has been made to date as its free amine and as its methanesulfonate salt. If tested in this anti-convulsant electroshock test, either as its free amine or as a salt thereof such as the hydrochloride of its methanesulfonate salt, we are reasonably sure that such compound, U-53,739, would also show a significantly low $ED_{50}$ number in this anti-convulsant test so that one could reasonably conclude that this trans-stereo compound U-53,739 would also have significant anti-convulsant activity.

However, as shown by Example 7 hereinabove the cis- stereo compound, U-54,494 (Compound 4 in Example 7) as its hydrochloride salt had no analgesic activity at the highest dose tested. In contrast, this trans-stereo form compound, U-53,739, as its free amine and as its methanesulfonate salt had the following analgesic test $ED_{50}$ numbers:

| Compound | Analgesic Screen Test. $ED_{50}$ (mg/kg) | | |
|---|---|---|---|
| | Flick | Pinch | HCl Writhing |
| U-53,739 | 2.4 | 2.1 | 6.0 |
| U-53,739, methanesulfonate | — | — | 6 |

The blanks indicate that these test with this salt compound were not run to our knowledge.

The above data and statements indicate that the analgesic activity property resides essentially exclusively in the trans-stereo compound, U-53,739. The cis- stereo compound, U-54,494 (Compound 4 in Example 7 hereinabove) has no analgesic property at the highest dose tested.

The presence of anti-convulsant activity in the cis- and trans-stereo form compound, U-54,494 (Compound 4 in Example 7 hereinabove), in the absence of analgesic activity is believed to be surprising and unpredictable because (1) pharmacological activities are most often stereoselective and, (2) as between various cis- and trans-stereo forms of a compound one of ordinary skill in the pharmacology art would expect the anti-convulsant activity to be present only in the same stereo form of a compound that also expesses the CNS depressant (analgesic or sedative) property. In contrast the compound cis-3,4-dichloro-N-methyl-N-[2-(1-pyrrolidinyl)-cyclohexyl]benzamide, U-54,494, was found to have potent anti-convulsant activity with no analgesic or sedative activity at the highest dose tested. This unique anti-convulsant drug activity of the U-54,494 compound should make the compound of value to physicians who whish to treat their patients against possible convulsant maladies while minimizing analgesic or sedatve side effects.

EXAMPLE 9

A more recent scale up preparation of cis-3,4-dichloro-N-methyl-N-[2-(1-pyrrolidinyl)cyclohexyl]-benzamide, as its hydrochloride salt was done as follows:

A. Preparation of ethyl/methyl cis-2-(1-pyrrolidinyl)cyclohexane carboxylate

To 411 ml. of benzene there was added 100 g. (578.5 mmol) of ethyl/methyl 2-cyclohexanone carboxylate (note: the ethyl/methyl 2-cyclohexanone carboxylate contains about 40 percent of the corresponding methyl ester) and 49 ml. (578.5 mmol) of pyrrolidine, and the resulting mixture was heated under a nitrogen atmosphere under reflux, using a water separator, overnight, during which time about 8.5 ml. of water was collected to form the intermediate, ethyl/methyl 2-(1-pyrrolidinyl)-1-cyclohexenyl carboxylate.

The reaction mixture was transferred to a 2 liter Parr bottle and 5.875 g. of platinum oxide was added. The mixture was hydrogenated at about 40 pounds hydrogen pressure for 4.5 hours, then another 2.093 g. of fresh platinum oxide was added and the mixture was hydrogenated overnight. The resulting hydrogenated reaction mixture was filtered through a wet (ethyl acetate) filter aid (Celite ®) and rinsed with ethyl acetate. The filtrate was transferred to a separatory funnel where the organic layers were extracted with 117.5 ml. of 6N hydrochloric acid and 25 ml. of water. The aqueous extracts were combined, washed with 200 ml. of ethyl acetate. then cooled in an ice bath, and then slowly treated with 60 ml. of 45 percent (w/v) aqueous potassium hydroxide solution. The aqueous phase was extracted with two 200 ml. portions of diethyl ether, the organic liquid phase was rinsed with one 100 ml. portion of brine (NaCl) solution. The organic extracts were combined and dried over magnesium sulfate, filtered and evaporated under reduced pressure to obtain a light yellow liquid residue which was fractionated through a short Vigreaux column to give 91.3 g. (415.6 mmol), (70.7 percent yield) of the intermediate, ethyl/methyl cis-2-(1-pyrrolidinyl)cyclohexane carboxylate, b.p. 96°-108° C. at 0.4 mm Hg. The nuclear magnetic resonance (NMR) spectrum of a sample of this material was consistent with the named structure.

B. Preparation of Cis-[2-(1-pyrrolidinyl)cyclohexyl]-carbonylhydrazide dihydrochloride A 91.3 g. (0.4156 mole) portion of the ethyl-methyl 2-(1-pyrrolidinyl)cyclohexanecarboxylate ester from part A hereinabove and 105.264 g. (2.105 moles) of hydrazine monohydrate in 840 ml. of absolute ethanol were reacted under a nitrogen atmosphere at reflux for about four days to ensure complete reaction.

The resulting reaction mixture was allowed to cool to room temperature and evaporated under reduced pressure until an oil residue was obtained. The oil residue was transferred to a separatory funnel with 969 ml. of methylene chloride. The organic liquid phase was rinsed with two 100 ml. portions of water, filtered through sodium sulfate, and concentrated under reduced pressure to obtain 79.4 g. of an amber liquid (0.376 mole) of the sub-titled crude compound.

This crude product was dissolved in 820 ml. of diethyl ether, and treated slowly with 271 ml. of 3.48N hydrochloric acid in diethyl ether. A thick gum formed. The liquid of the mixture was decanted off, and the gum was dissolved in 315 ml. of hot (50° C.) methanol. The mixture was cooled, treated with 442 ml. of diethyl ether to form a white precipitate, which was stored at 5° C. The resulting subtitled hydrazide dihydrochloride weighed 42.522 g. (105.2 mmol; 25.3 percent yield), m.p. 222°-223.8° C. A previously reported m.p. for this compound was 222°-224° C.

C. Preparation of cis-2-(1-pyrrolidinyl)cyclohexaneamine.

A 75.46 g. portion (186.6 mmol) of the 2-(1-pyrrolidinyl)cyclohexanecarbonyl hydrazide from part B hereinabove in 140 ml. of water, cooled in an ice bath, was slowly treated with 20.19 g. (292.7 mmol) of sodium nitrite in 35 ml. of water over about 0.5 hour at −2° to +10° C. The mixture was stirred in a methanol-/ice bath (−4° C.) for 0.5 hour, during which time a precipitate formed. The 42.4 ml. of 12N hydrochloric acid was slowly added and the mixture was slowly heated to 70° C.; a brown gum formed. After nitrogen evolution ceased the mixture was heated to 95° C. for one hour to ensure complete reaction, and then was cooled in an ice bath, and 212 ml. of a 15 percent w/v sodium hydroxide solution was added. The resulting mixture was extracted with three 200 ml. portions of diethyl ether, the organic extracts were washed with 100 ml. of brine solution, then combined and dried over magnesium sulfate at room temperature, filtered and the filtrate concentrated under reduced pressure to obtain 39.199 g. of the crude sub-titled amine, as a brown liquid whose infrared (IR) spectrum was consistent with the assigned structure. Fractionation through a short Vigeaux column gave 40.63 g. (58 percent yield) of the sub-titled compound, b.p. 61°-67° C. at 1 mm Hg as a colorless liquid.

D. Preparation of Cis-N-methyl-N-[2-(1-pyrrolidinyl)cyclohexane]amine

A 40.6 g. (241.4 mmol) portion of the cis-[2-(1-pyrrolidinyl)cyclohexane]amine, prepared as described in part c, in 500 ml. of ethyl formate was heated under reflux for about 18 hours. The reaction mixture was concentrated under reduced pressure to give a clear oil which was dissolved in 200 ml. of THF. This resulting solution was added by way of a dropping funnel to a mixture of 40.57 g. of lithium aluminum hydride in 2030 ml. of diethyl ether. The resulting mixture was heated to reflux for six hours and then allowed to stand overnight. The mixture was cooled in an ice bath and the excess lithium aluminum hydride in the mixture was decomposed by the slow addition of 40 ml. of water, 40 ml. of water, 40 ml. of 15 percent w/v sodium hydroxide in water solution and 120 ml. of water. A white slurry formed which was stirred for about 0.5 hour and filtered. The white solid was washed with diethyl ether and the combined filtrates were concentrated under reduced pressure to give 44 g. of a colorless liquid, which was diluted to obtain 34.620 g. of the sub-titled cis-N-methyl-N-[2-(1-pyrrolidinyl)cyclohexane]amine (189.9 mmol) (78.7 percent yield), b.p. 60°–64° C./0.6–0.8 mm Hg.

E. Preparation of cis-N-methyl-N-[2-(1-pyrrolidinyl)cyclohexyl]-3,4-dichlorobenzamide, and its hydrochloride salt A 13.73 g. (75.3 mmol) potion of the cis-N-methyl-N-[2-(1-pyrrolidinyl)cyclohexane]amine from part D above in 1500 ml. of diethyl ether was mixed with 10.5 ml. of triethylamine with stirring. To this mixture there was slowly added 15.772 g. (75.3 mmol) of 3,4-dichlorobenzoyl chloride in 188 ml. of diethyl ether, while the reaction mixture was maintained under a nitrogen atmosphere via a dropping funnel. The white slurry which formed was stirred for one hour to ensure complete reaction.

The white slurry reaction mixture was cooled in an ice bath and treated slowly with 377 ml. of 1N potassium bicarbonate solution. The mixture cleared and was transferred to a separatory funnel with a little added diethyl ether. The organic phase was washed with 377 ml. of brine solution which was backwashed with 500 ml. of diethyl ether. The organic extracts were combined and dried with magnesium sulfate at room temperature. The dried organic liquid layer was filtered and evaporated under reduced pressure to leave as residue 27.6 g. of the titled-benzamide as a clear oil.

This clear oil was dissolved in 750 ml. of diethyl ether and then while mixing there was slowly added 37.5 ml. of 3.48N hydrogen chloride in diethyl ether. The acidic mixture was evaporated under reduced pressure to leave 38.7 g. of the titled-benzamide hydrochloride salt as a white solid.

The above prepared titled-benzamide hydrochloride salt was further purified by recrystallization from methanol/diethyl ether. A batch, 38.7 g., of the titled-benzamide hydrochloride salt was crytallized from a mixture of 150 ml. of methanol and one liter of diethyl ether. After storing the mixture at 5° C. there was obtained 21.222 g. of the titled-benzamide hydrochloride salt, m.p. 225°–226° C. (decomposed; discolored at 223° C.).

The analytical sample of the cis-N-methyl-N-[2-(1-pyrrolidinyl)cyclohexyl]-3,4-dichlorobenzamide hydrochloride salt, prepared as described herein, had a m.p. of 224.5°–225.5° C. (decomposed) and had an elemental analysis as follows:

| | Anal. Calcd. for $C_{18}H_{25}N_2OCl_3$ (MW 391.77) | | | |
|---|---|---|---|---|
| | C | H | N | Cl |
| % theory | 55.19 | 6.43 | 7.15 | 27.15 |
| % found | 55.11 | 6.68 | 7.01 | 27.11 |

The ultraviolet (UV), IR and NMR spectra for this sample of the compound were consistent with the named compound.

GENERAL FORMULAS

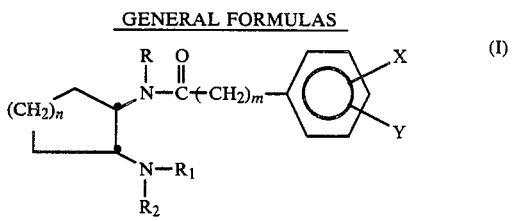

SCHEME I

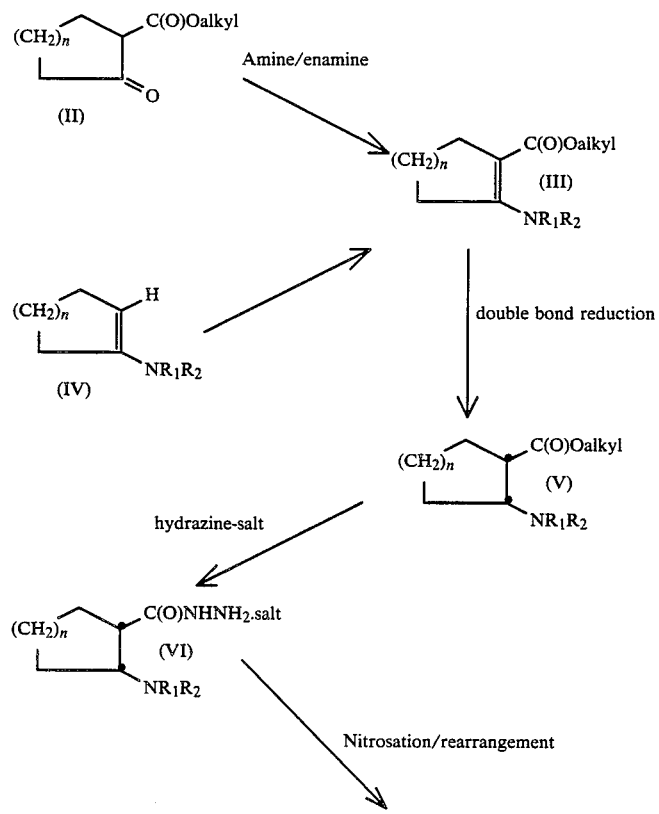

SCHEME I -continued

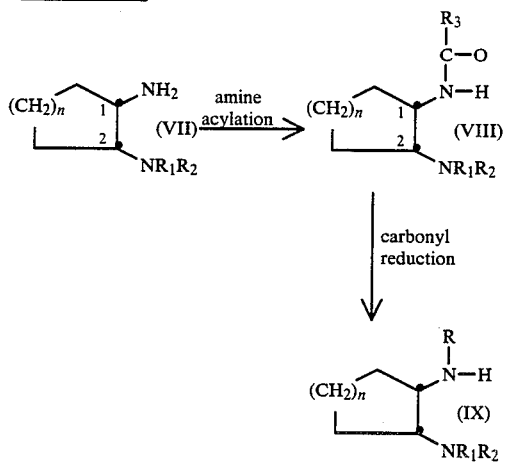

SCHEME II

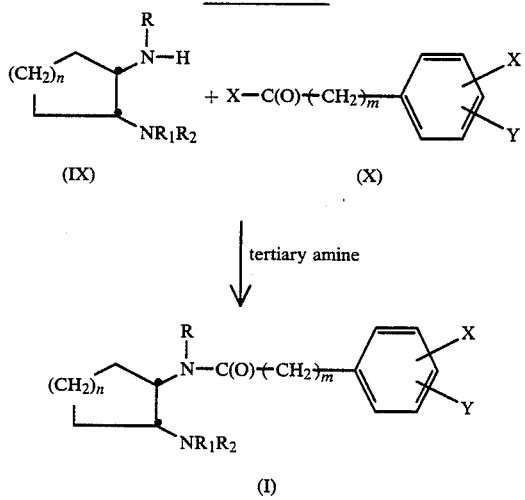

We claim:

1. A method for preventing or treating Central Nervous System (CNS) seizures in a warm-blooded animal patient which comprises administering to such patient suffering from seizures or likely to experience seizures an amount of cis-3,4-dichloro-N-methyl-N-[2-(1-pyrrolidinyl)cyclohexyl]benzamide, or a pharmaceutically acceptable salt thereof, which amount is effective to prevent or reduce the effects of such CNS seizure disorder in said patient.

2. A method as defined in claim 1 wherein the CNS seizure-preventing or blocking compound is cis-3,4-dichloro-N-methyl-N-[2-(1-pyrrolidinyl)cyclohexyl]-benzamide hydrochloride.

3. A compound selected from the group consisting of cis-3,4-dichloro-N-methyl-N-[2-(1-pyrrolidinyl)cyclohexyl]benzamide, or a pharmaceutically acceptable salt thereof.

4. A compound according to claim 3 which is cis-3,4-dichloro-N-methyl-N-[2-(1-pyrrolidinyl)cyclohexyl]-benzamide hydrochloride.

5. A composition for preventing or treating Central Nervous System (CNS) seizures in a warm-blooded animal patient which comprises cis-3,4-dichloro-N-methyl-N-[2-(1-pyrrolidinyl)cyclohexyl]benzamide, or a pharmaceutically acceptable salt thereof, as an active ingredient in an amount sufficient to stop or reduce a CNS seizure condition in combination with a pharmaceutically acceptable carrier.

6. A composition as defined in claim 5 wherein the CNS seizure-preventing or -blocking compound is cis-3,4-dichloro-N-methyl-N-[2-(1-pyrrolidinyl)cyclohexyl]benzamide hydrochloride.

* * * * *

UNITED STATES PATENT OFFICE
CERTIFICATE OF CORRECTION

Patent No. 4,801,604　　　　　　　　　Dated January 31, 1989

Inventor(s) P.F. VonVoightlander, et al.

It is certified that error appears in the above-identified patent and that said Letters Patent is hereby corrected as shown below:

Lead page, second column "cycloalophatic" should read -- cycloaliphatic --.
Column 1, line 1 "CIS-N-(2-Amino" should read -- CIS-N-[(2-Amino --.
Column 3, line 64 "supositories" should read -- suppositories --.
Column 4, line 7 "nd" should read -- and --.
Column 4, line 40 "preparation", second occurrence, to -- preparations --.
Column 6, line 65 "crystallized" should read -- recrystallized --.
Column 7, line 29 "kin" should read -- in --.
Column 8, line 38 "(methanol/ether" should read -- (methanol/ether) --.
Column 10, line 50 "test" should read -- tail --.
Column 10, line 58 "were" should read -- are --.
Column 10, line 59 "with" should read -- which --.
Column 12, line 22 "U-54,484" should read -- U-54,494 --.
Column 12, line 34 "of" should read -- or --.
Column 13, line 13 "whish" should read -- wish --.
Column 13, line 37 "2.093" should read -- 2.93 --.
Column 13, line 46 "acetate. then" should read -- acetate, then --.
Column 13, line 63 "ethyl-methyl" should read -- ethyl/methyl --.
Column 14, lines 62-63 "40 ml. of water, 40 ml. of water, 40 ml. of 15 percent" should read -- 40 ml. of water, 40 ml. of 15 percent --.
Column 15, line 1 "diluted" should read -- distilled --.

Signed and Sealed this

Fifteenth Day of August, 1989

Attest:

DONALD J. QUIGG

Attesting Officer　　　　Commissioner of Patents and Trademarks